(12) United States Patent
Akpinar (10) Patent No.: US 9,510,811 B2
(45) Date of Patent: Dec. 6, 2016

(54) MEDICAL OCCLUSION DEVICE (71) Applicant: Occlutech Holding AG, Schaffhausen (CH)

(72) Inventor: Mehmet Hakan Akpinar, Istanbul (TR)

(73) Assignee: Occlutech Holding AG, Schaffhausen (CH)

( * ) Notice: Subject to any disclaimer, the term of this patent is extended or adjusted under 35 U.S.C. 154(b) by 0 days.

(21) Appl. No.: 14/354,530

(22) PCT Filed: Nov. 23, 2012

(86) PCT No.: PCT/EP2012/073526
§ 371 (c)(1),
(2) Date: Apr. 25, 2014

(87) PCT Pub. No.: WO2013/076276
PCT Pub. Date: May 30, 2013

(65) Prior Publication Data
US 2014/0277119 A1    Sep. 18, 2014

Related U.S. Application Data

(60) Provisional application No. 61/563,161, filed on Nov. 23, 2011.

(51) Int. Cl.
*A61B 17/08*    (2006.01)
*A61B 17/00*    (2006.01)
*A61B 17/12*    (2006.01)

(52) U.S. Cl.
CPC ..... *A61B 17/0057* (2013.01); *A61B 17/12109* (2013.01); *A61B 17/12122* (2013.01);
(Continued)

(58) Field of Classification Search
CPC .... A61B 17/1022; A61B 17/12168–17/12177;
A61B 17/1214; A61B 17/0057; A61B 17/12122; A61B 17/12027; A61B 17/12031; A61B 17/12099; A61B 17/12104; A61B 17/12109; A61B 17/12113; A61B 17/12145; A61B 12/1215; A61B 2017/00526; A61B 2017/00575; A61B 2017/00579; A61B 2017/00592; A61B 2017/00597; A61B 2017/00606; A61B 2017/00601; A61B 2017/00628; A61B 2017/00637; A61B 2017/00659
(Continued)

(56) References Cited

U.S. PATENT DOCUMENTS

2007/0167980 A1* 7/2007 Figulla et al. ............... 606/213
2008/0188873 A1* 8/2008 Speziali ....................... 606/144
2013/0131717 A1* 5/2013 Glimsdale ................... 606/213

FOREIGN PATENT DOCUMENTS

DE    102006013770 A1    9/2006
EP          2387950 A1    11/2011
WO    WO2008/040555 A2    4/2008

OTHER PUBLICATIONS

WIPO, European International Search Authority, International Search Report mailed Feb. 5, 2013 in International Patent Application No. PCT/EP2012/073526, 7 pages.

* cited by examiner

*Primary Examiner* — Todd E Manahan
*Assistant Examiner* — Erich Herbermann
(74) *Attorney, Agent, or Firm* — Inskeep IP Group, Inc.

(57) ABSTRACT

A medical implantable occlusion device (100, 200, 300) is disclosed comprising a braiding (101) of at least one thread, the braiding having an unloaded relaxed state and a stretched state and comprising an expanded diameter portion (102) spanning a distal surface (180) forming the distal end (181)

(Continued)

of said device, wherein the braiding is continuous at the distal surface, a tubular member (103) extending along a longitudinal axis (104), the tubular member having a distal portion (105) transitioning into the expanded diameter portion and an opposite proximal portion (106), wherein the tubular member is tapered towards the expanded diameter portion along the longitudinal axis.

15 Claims, 8 Drawing Sheets

(52) U.S. Cl.
CPC .. *A61B 17/12172* (2013.01); *A61B 17/12177* (2013.01); *A61B 2017/00575* (2013.01); *A61B 2017/00592* (2013.01); *A61B 2017/00597* (2013.01)

(58) Field of Classification Search
USPC ............... 606/191, 200, 213–215; 623/23.72
See application file for complete search history.

MEDICAL OCCLUSION DEVICE

RELATED APPLICATIONS

This application is the U.S. National Phase of and claims priority to International Patent Application No. PCT/EP2012/073526, International Filing Date Nov. 23, 2012, entitled Medical Occlusion Device, which claims benefit of U.S. Provisional Application Ser. No. 61/563,161, filed Nov. 23, 2011 entitled Occlusion Device; both of which are incorporated herein by reference in their entireties.

FIELD OF THE INVENTION

This invention pertains in general to the field of medical occlusion devices. More particularly the invention relates to an occlusion device for occlusion during structural heart repair procedures, such as aortic valve replacement using the Trans Apical Placement (TAP) Procedure.

BACKGROUND OF THE INVENTION

Transapical access can be a desirable option for minimally invasive procedures in the heart, such as aortic valve reoperation, Mitral valve and annulus repair/replacement and reoperation, ablation of arrhythmia foci in cardiac chambers, Left atrial appendage closure, aortic endo-grafting for aneurysms, percutaneous coronary intervention, VSD closure, and ablative LA and LV procedures. The transapical access may provide improved device control with a shorter distance to the target site, less stored tension or slack in the delivery system, access to all left sided structures and aorta. This is in contrast to some transfemoral access disadvantages such as a longer distance to the target with possibly less control and stored tension and slack in the access system, and all left sided structures may not be accessible.

When the transapical access procedure is completed previous techniques that provides for closure of the access opening in the apex of the left ventricle includes drawing the surrounding tissue at the opening together by sutures or using more complex structures that applies tension to the tissue to be drawn together around the access hole.

A problem with prior art is local shear forces that may cause myocardial damage and tearing by such techniques. This may in particular occur if the transapical procedure requires a sheath of a larger dimension such as 18, 24 or 32 Fr, or larger, where the tissue around the resulting access opening needs to be pulled together more to close the opening. This may also cause more bleeding and a lengthier procedure to control the bleeding, e.g. by additional suturing. Tearing, damage or rupture at the aortic root require subsequent repair and even a complete root replacement operation.

A further problem is the high level of precision and skill required using the previous closure techniques, that use a multitude of operational steps involving significantly complex steps, requiring more time, and/or with a potential risk of insufficient closure of the access site.

The above problems may have dire consequences for the patient and the health care system. Patient risk is increased.

Thus, there is a need for a closure solution which allows safe and easy closure of the transapical access opening with consistent and predictable results.

A compact closure device is also desirable for quick and easy delivery, for example via a catheter, and for occupying less space in the body, expose a minimum of foreign material to the surrounding anatomy and blood stream, and thereby reducing chance of interference with bodily functions.

Further, a degree of flexibility of a transapical access closure device to accommodate anatomical movements without fatigue or risk of loosening from the implantation site during an ingrowth period is also a desired characteristic of such device.

Hence, an improved device would be advantageous and in particular allowing for improved occlusion of transapical access openings, procedural effectiveness, and/or patient safety would be advantageous.

SUMMARY OF THE INVENTION

Accordingly, embodiments of the present invention preferably seeks to mitigate, alleviate or eliminate one or more deficiencies, disadvantages or issues in the art, such as the above-identified, singly or in any combination by providing a device and a method according to the appended patent claims.

Embodiments of the present invention may be well suited for the selective occlusion of a hole, lumen, channel, cavity, vessel or the like. One particular example, without limitation, of such a condition is a transapical access opening, Patent Ductus Arteriosus (PDA). Another example is a vessel, lumen, channel, hole or shunt, through which blood flows from one vessel to another vessel such as an Atrial Septal Defect (herein after ASD) or a Ventricular Septal Defect (herein after VSD). Other examples could be an Arterial Venous Fistula (AVF), Arterial Venous Malformation (AVM), a Patent Foramen Ovale (PFO), or a Para-Valvular Leak (PVL).

According to a first aspect of the invention a medical implantable occlusion device is provided comprising a braiding of at least one thread, the braiding having an unloaded relaxed state and a stretched state and comprising an expanded diameter portion spanning a distal surface forming the distal end of said device, wherein the braiding is continuous at the distal surface, a tubular member extending along a longitudinal axis, the tubular member having a distal portion transitioning into the expanded diameter portion and an opposite proximal portion, wherein the tubular member is tapered towards the expanded diameter portion along the longitudinal axis.

According to a second aspect of the invention a medical method of occluding an opening in a cardiovascular system using a device according to the first aspect is provided, comprising inserting said device in a collapsed state into the opening, expanding and releasing the device in the opening, thus anchoring the device in the opening for occluding the latter by the device.

According to a third aspect of the invention a medical method of occluding a transapical access opening is provided, comprising creating an opening in the apex of the heart ventricle, performing a procedure through the transapical access, inserting an occlusion device in the opening to occlude the opening.

Further embodiments of the invention are defined in the dependent claims, wherein features for the second and subsequent aspects of the invention are as for the first aspect mutatis mutandis.

Some embodiments of the invention provide for sutureless closure of transapical access openings.

Some embodiments of the invention provide for minimized myocardial damage and minimized tearing of tissue around the transapical access opening.

Some embodiments of the invention provide for a reliable closure approach that will reduce operation time, abate blood loss, and simplify complex structural heart repair procedures, ultimately enabling a conversion from surgical procedures to fully percutaneous catheter lab-based procedures.

Some embodiments of the invention provide for a medical implantable occlusion device that conform to different instrument sizes.

Some embodiments of the invention provide for minimally invasive access.

Some embodiments of the invention provide for a medical implantable occlusion device that comply with the beating heart so as not to interfere with wall motion and expose a minimal amount of foreign material to the blood stream.

Some embodiments of the invention provide for flexible positioning of a medical implant to varying anatomical sites in a body of a human or animal.

Some embodiments of the invention also provide for secure attachment of a medical implant in a patient's cardiovascular system.

Some embodiments of the invention provide for a compact medical implant with maintained flexibility.

Some embodiments of the invention provide for a medical implant that can be safely delivered to a treatment site in a patient.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements. The elements of the figures may not be in scale in relation to each other.

The following description focuses on an embodiment of the present invention applicable to a transapical plug, or a PDA plug. However, it will be appreciated that the invention is not limited to this application but may be applied to many other medical implantable devices, including for example filters, stents, Left Atrial Appendage (LAA) occluders, aneurysm treatment devices, grafts, etc.

Figure 1:
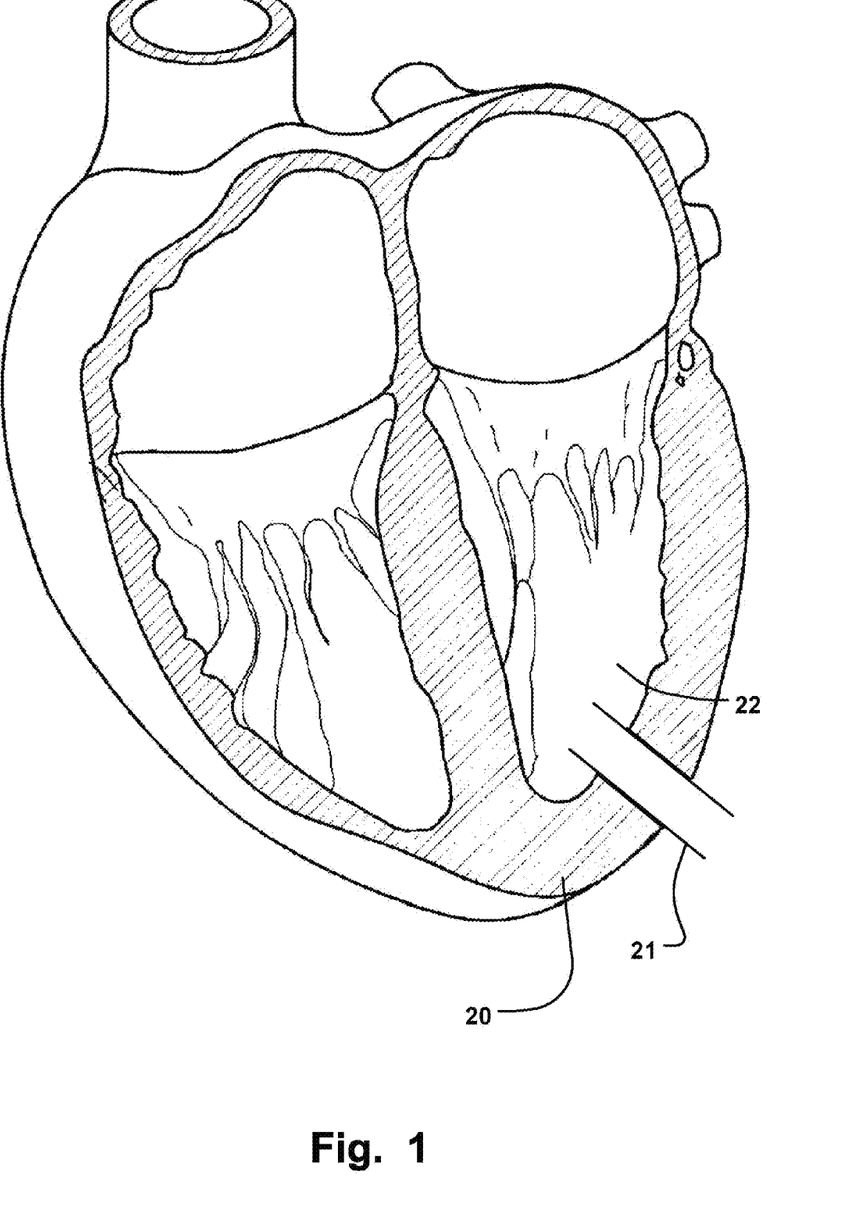
FIG. 1 is an illustration of how transapical access is created in the heart.

FIG. 1 is a cross-section schematic of the heart, where access has been created trough the apex 20 of the left ventricle with a instrument 21, such as a catheter or the like for performing procedures in the heart such as described in the background of the invention via the transapical access opening.

FIG. 1 shows a medical implantable occlusion device 100 according to an embodiment of the invention. The device 100 comprises a mesh or braiding 101 of at least one thread. The braiding 101 may be formed from one thread or several. The device 100, or more particularly the braiding 101, has an unloaded relaxed state and a stretched state. Thus, in the relaxed state, wherein the device 100 has a shape as depicted in FIG. 1, no external force acts on the device 100. The device 100 may be stretched and thereby exhibit a smaller cross-section, in order to fit inside a delivery device such as a catheter. The device 100 may be self-expandable between the stretched state and the relaxed state, i.e. when the device 100 is removed from the confinement of the catheter the cross-section of the device 100 returns to its originally defined value in the unloaded relaxed state. The device may be self-expandable due to an inherent elasticity of the threads in the braiding. The device may also have a shape memory, e.g. triggerable to go to the relaxed state at a switching temperature, such as body temperature. Alternatively, or in addition, in other embodiments of the implantable device, expansion devices (not shown), such as inflatable balloons, may be used to bring the device from the collapsed state to the expanded, relaxed state.

The shape of the device 100 in the relaxed state may be defined in a heat treatment procedure of the device 100 or more particularly of the braiding 101. The dimensions of the device 100 in the relaxed state are defined in the heat treatment procedure if the braiding.

The entire device 100-400 (c.f. FIGS. 5, 7, 9-10) may be comprised of a single, continuous braiding 101. The braiding 101 may be made of a material suitable for implanting in a human or animal body, and suitable for being formed in a heat treatment procedure to a desired shape in the unloaded relaxed state and also in the stretched state. For example NiTinol may be used as a material for the device 100-400. However, suitable materials for embodiments of the braiding are various and include shape memory materials, metal, superelastic alloys (such as NiTinol), or polymers, such as degradable polymers.

The braiding 101 comprises an expanded diameter portion 102, and a tubular member 103 extending along a longitudinal axis 104. The tubular member 103 has a distal portion 105 that is connected and transitions to the expanded diameter portion 102, and an opposite proximal portion 106. The expanded diameter portion 102 spans a distal surface 180 that forms the distal end 181 of the device 100. The braiding 101 is continuous at the distal surface 180 to thereby form a closed braiding at the distal end 181 of the device 100.

Figure 6:
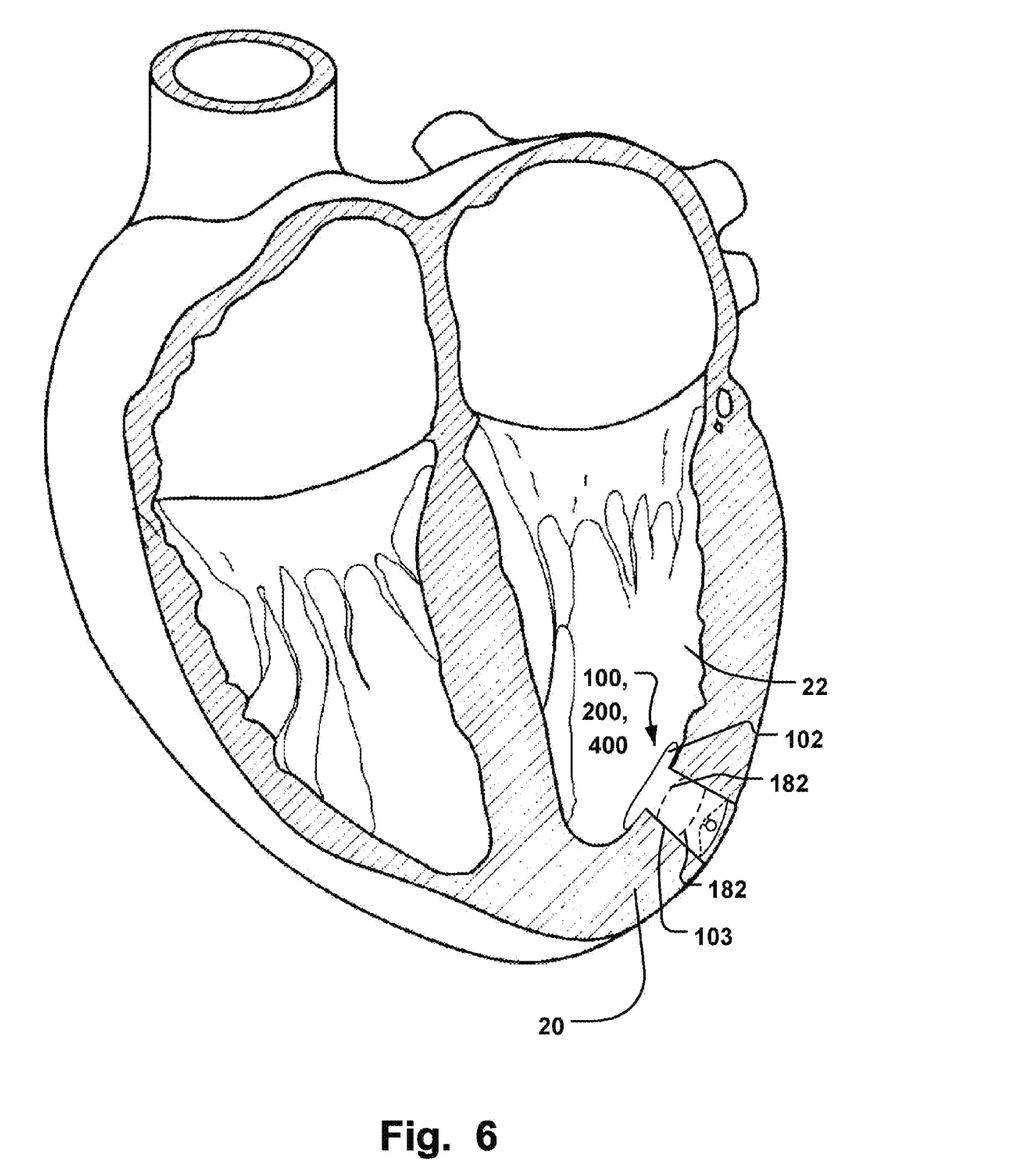
FIG. 6 is an illustration of occluding a transapical access opening with a medical implantable occlusion device according to an embodiment of the invention.
Figure 7:
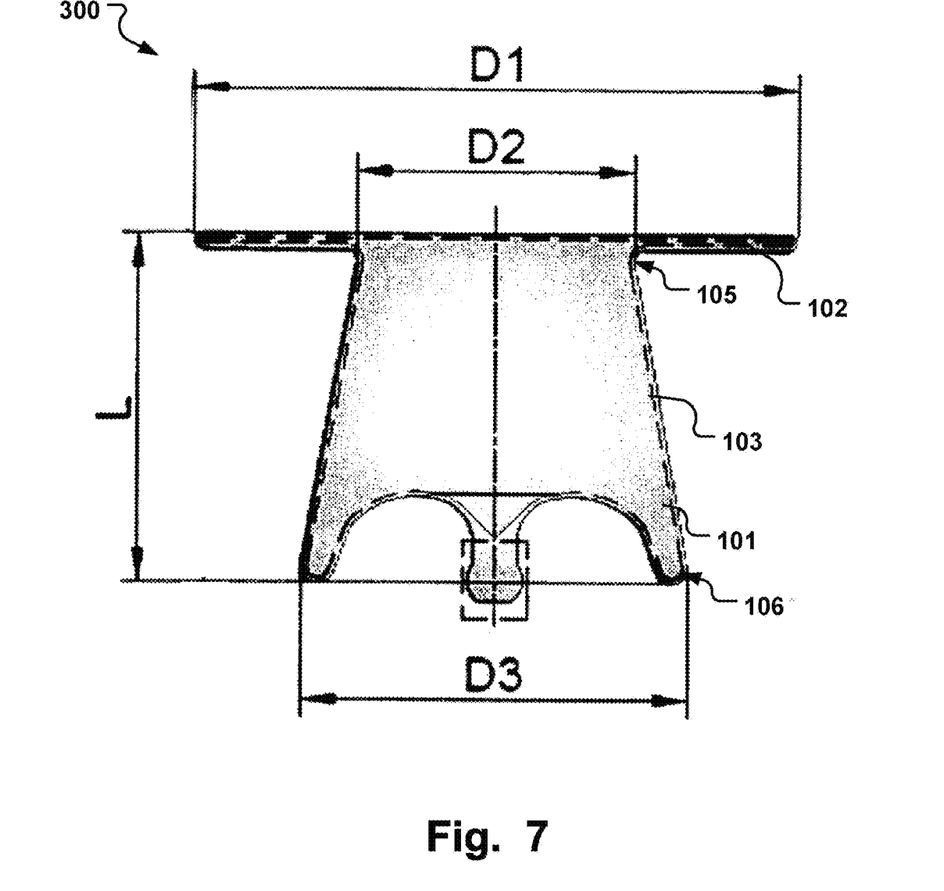
FIG. 7 is an illustration of a medical implantable occlusion device according to an embodiment of the invention in a side view.

The tubular member 103 is tapered towards the expanded diameter portion 102 along the longitudinal axis 104. The tapered shape is now described further with reference to FIG. 7, showing an embodiment of the medical occlusion device 300. The maximum diameter (D3) of the proximal portion 106 is thereby larger than the maximum diameter (D2) of the distal portion 105. When positioned in the opening to be occluded, the tapered shape towards the expanded diameter portion 102 create an increased force acting on the walls of the opening to be occluded, i.e. a force acting in direction of the longitudinal axis 104 of the device 100-400 towards the expanded diameter portion 102. Thereby a compressive force is achieved, in comparison to a pure frictional force against the tissue wall of the opening in case the device is not tapered, or tapered in the other direction. The tapered shape, similar to a champagne cork, has a function similar to an oversized cork at one end, leading to improved retention in the opening, which provides increased holding force or locking feature of the device 100-400 in the opening. A pressure induced force component acting on the device 100-400 on the proximal portion 106 in a direction towards the expanded diameter portion 102 will contribute to an increased force acting from the tubular member 103 to the walls of the opening, creating a counter force acting from the walls of the opening towards the proximal portion 106 thereby cancelling the aforementioned pressure induced force component. This thereby improves the sealing and secure occlusion of the opening. Thus a secure occlusion is achieved even before the device is securely covered with endothelia and tissue integrated with the surrounding tissue. Secure occlusion is provided without the need for drawing the opening together by applying force to the tissue surrounding the opening, which as mentioned, is an more aggressive way of closing the opening that cause more bleeding and possibly re-suturing of the opening, leading to a more time consuming procedure. As seen in FIG. 6, the device 100-400 is positioned with the expanded diameter portion 102 in the left heart chamber so that the pressure of the blood acts on the expanded diameter portion 102 in a direction towards the proximal portion 106. Any pressure in the other direction, will be counteracted by the pressure on the expanded diameter portion and the tapered shape of the tubular member 103.

The ratio by dividing a maximum diameter of the proximal portion 106 with a maximum diameter of the distal portion 105, may be set to a value more than 1.1. This may allow for advantageous sealing of the occlusion device 100-400 against the tissue walls of the opening. A value below 1.1 may reduce such sealing effectiveness.

By having a continuous and closed braiding at the distal end 181 of the device 100, there is no element of the expanded diameter portion that protrudes from its distal surface 180 into the heart chamber 22, thereby minimizing disturbance of blood flow, and bodily material collecting at any protruding portion or blood cloths. In particular the expanded diameter portion is substantially flat and has a diameter larger than an ostium of the shunt into which it is placed. Thus the rim of the periphery of the expanded diameter portion 102 may advantageously engage the tissue around the opening. See further below for discussion of the braiding comprising returning loops for allowing dispensing with the need for collecting the ends of the threads at the distal end 105.

The distal portion 105 may transition to a periphery of the expanded diameter portion 102 with a continuously increasing diameter along the longitudinal axis 104. The smallest diameter of the device 100-400 corresponds thereby to the maximum diameter of the distal portion 105. This provides for increased structural integrity of the device 100-400, e.g. such that the amount of possible displacement between expanded diameter portion 102 and tubular member 103 is limited and effectively controlled to improve and secure occlusion efficiency, such as in the transapical access opening, where the beating heart cause significant movement, while still having a flexibility of the expanded diameter portion 102 so that it can conform to various anatomical geometries. The structural integrity as described above in combination with the tapered shape provides for a particularly effective, improved and reliable occlusion of a transapical access opening.

As mentioned the device 100-400 is flexible to adapt to the transapical access opening. Hence the expanded diameter portion 102 may be flexible with respect to the tubular member 103 such that the expanded diameter portion 102 is moveable with an angle in relation to the longitudinal axis 104. The tubular member 103 and the expanded diameter portion 102 may be elastically stretchable relative each other along the longitudinal axis 104 whereby the device 100-400 is self-contracting.

Figure 2:
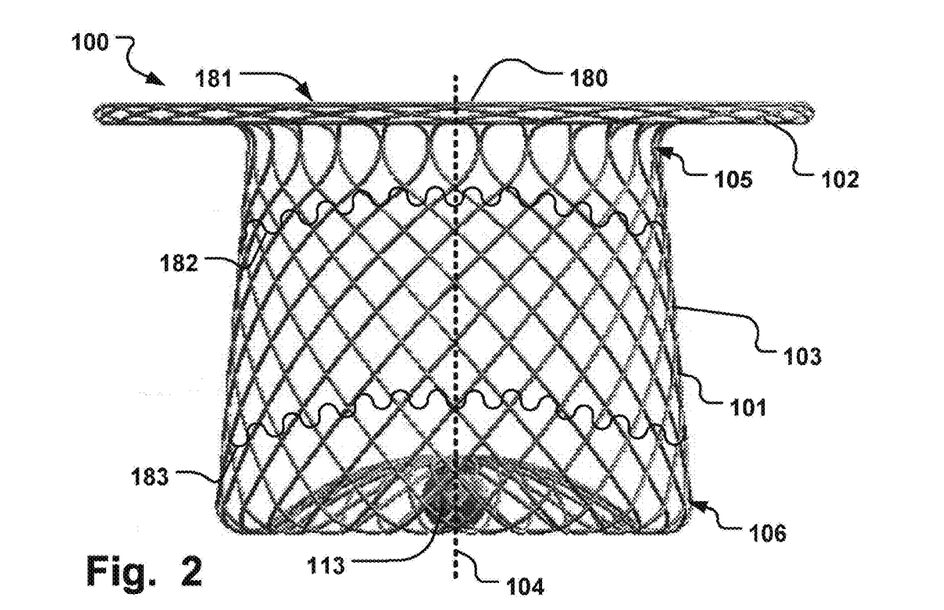
FIG. 2 is an illustration of a medical implantable occlusion device according to an embodiment of the invention in a side view.

The displacement of the connecting member 108 into the tubular member 103 provides a more compact device 100, as the entire length of the connecting member 108 may be sunk into the tubular member 103. FIG. 2 shows a side view of the device 100, where a connecting member 113 in the form of a spherical ball is provided at the proximal portion 106 for connecting to a mating socket.

Figure 5:
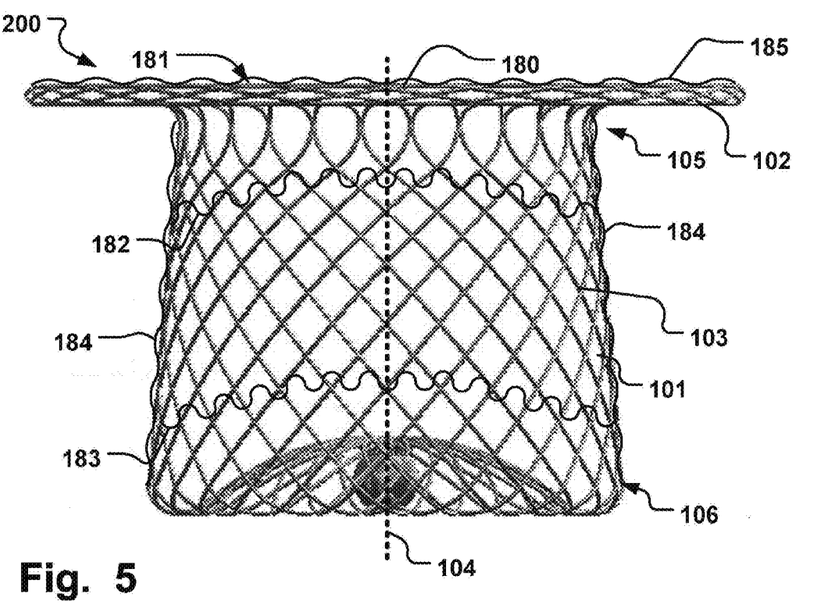
FIG. 5 is an illustration of a medical implantable occlusion device according to an embodiment of the invention in a side view.

The device 100-400 may comprise at least one planar and/or voluminous occluding member 182, 183, 184, 185, at the interior or exterior of the tubular member 103 to occlude a blood flow. The occluding member 182, 183, 184, 185, may also be provided by a coating process of the surface of the device 100-400. The occluding member may comprise biocompatible fibres or patches of for example of PET that support sealing of the blood flow through the device 100-400, and thereby the opening to be occluded immediately after implantation. Fibres or patches promote endothelialisation and accelerate occlusion. As seen in FIG. 1, the device 100 comprises occluding members 182, 183, inside the tubular member 103. FIG. 5 illustrates another embodiment where the device 200 comprises occluding members 184, 185, at the exterior or outside of the space contained by the tubular member 103. A particular exterior occluding member 185 covers the distal surface 180 of the expanded diameter portion 102.

The expanded diameter portion 102 may be concentric with respect to the tubular member 103. A symmetric shape of the device 100 may increase the flexibility of the expanded diameter portion 102 in relation to the tubular member 103. An asymmetric configuration may be suitable in particular anatomies to be occluded.

The expanded diameter portion 102 may be a disc shaped portion. The disc may be bent with its outer periphery closer towards the tubular portion than the center portion thereof, i.e. concave towards the proximal portion (not shown), or concave (not shown). Alternatively, it may have any shape suitable for the particular anatomy of the opening to be occluded.

Figure 3:
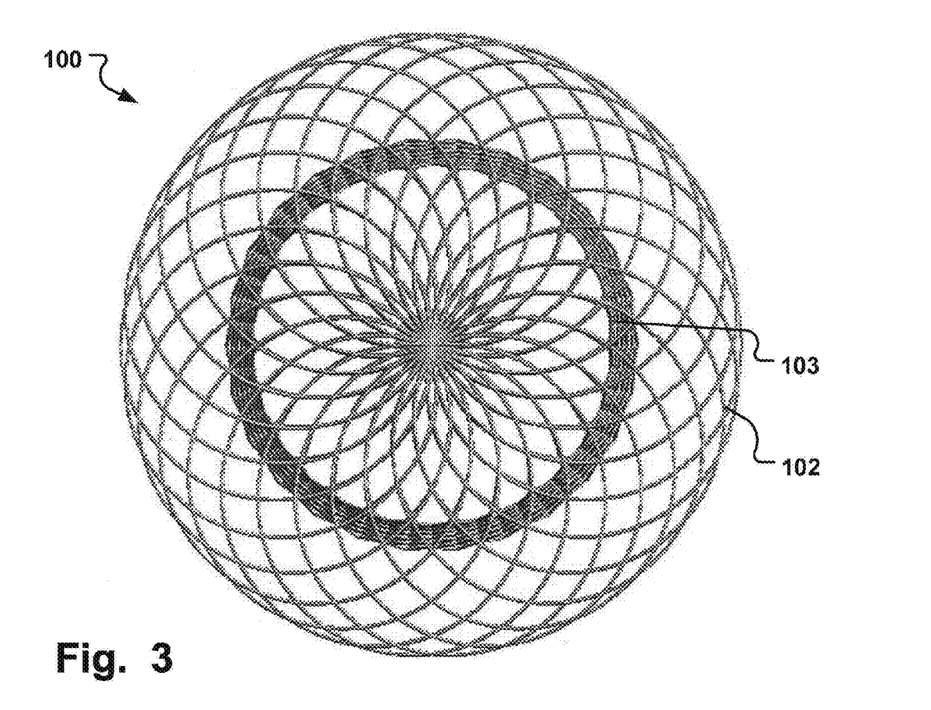
FIG. 3 is a top down view of the medical implantable occlusion device in FIG. 2.

The outer diameter (D1) of the expanded diameter portion 102 may be substantially larger than a diameter of the tubular member 103, as depicted in e.g. FIG. 3 or FIGS. 2, 7. An increased diameter (D1) may reduce the pressure exerted by the expanded diameter portion 102 on the tissue wall at the occlusion site, and decrease the risk of the device 100-400 being dislodged from the occlusion site. The diameter may be equivalent to the largest cross-section throughout the disclosure.

The proximal portion 102 may comprise a connecting member 113 for a delivery device (not shown). The delivery device may grasp the connection member 113 which may be spherical in shape, thus providing a pivoting motion of the device 100 in relation to the delivery device in combination with secure attachment. The ends of the at least one thread forming the braiding 101 may be fixed to the connecting member 113. The connecting member 113 may thus be a weld or any other attachment means for the threads of the braiding 101. The connecting member may comprise a threaded screw attachment (not shown) of female or male type for threaded attachment to a delivery device having corresponding threads.

The expanded diameter portion 102 may comprise returning loops of the at least one thread, meaning that opposite ends of the at least one thread forming the expanded diameter portion 102 are fixed to the connecting member 113. By having returning loops only one collection point for the ends of the at least one thread is needed. The connection member 113 may thus serve as a connection for these ends, thereby avoiding multiple connection points such as welds on the expanded diameter portion 102. Hence, a flat expanded diameter portion 102 may be provided, that increases the compactness of the device 100. Thereby no parts of the device 100 extend beyond the expanded diameter portion. By having such compact device 100, it may be easily positioned and manipulated at the target site. This is in contrast to cases having protruding parts at both the distal and proximal ends, which could not attain the same degree of compactness of the device.

Figure 4:
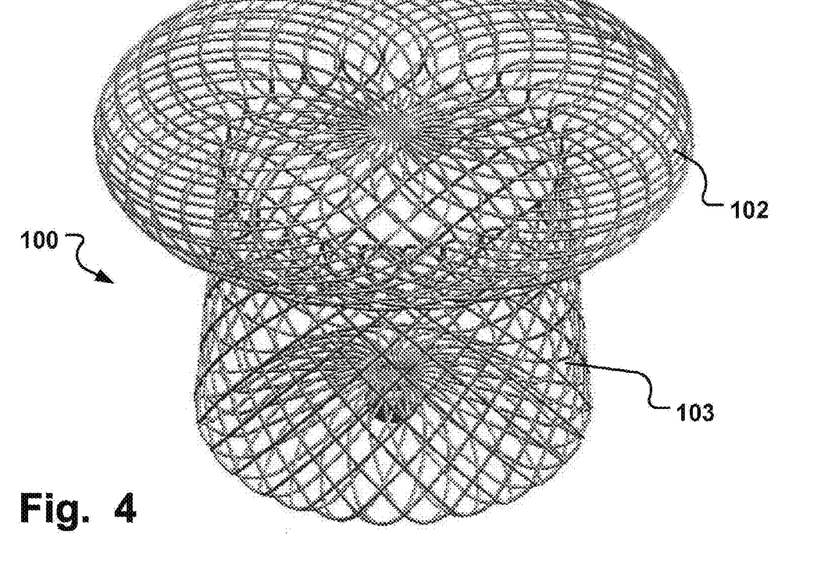
FIG. 4 is a perspective view the medical implantable occlusion device in FIG. 2.
Figure 9:
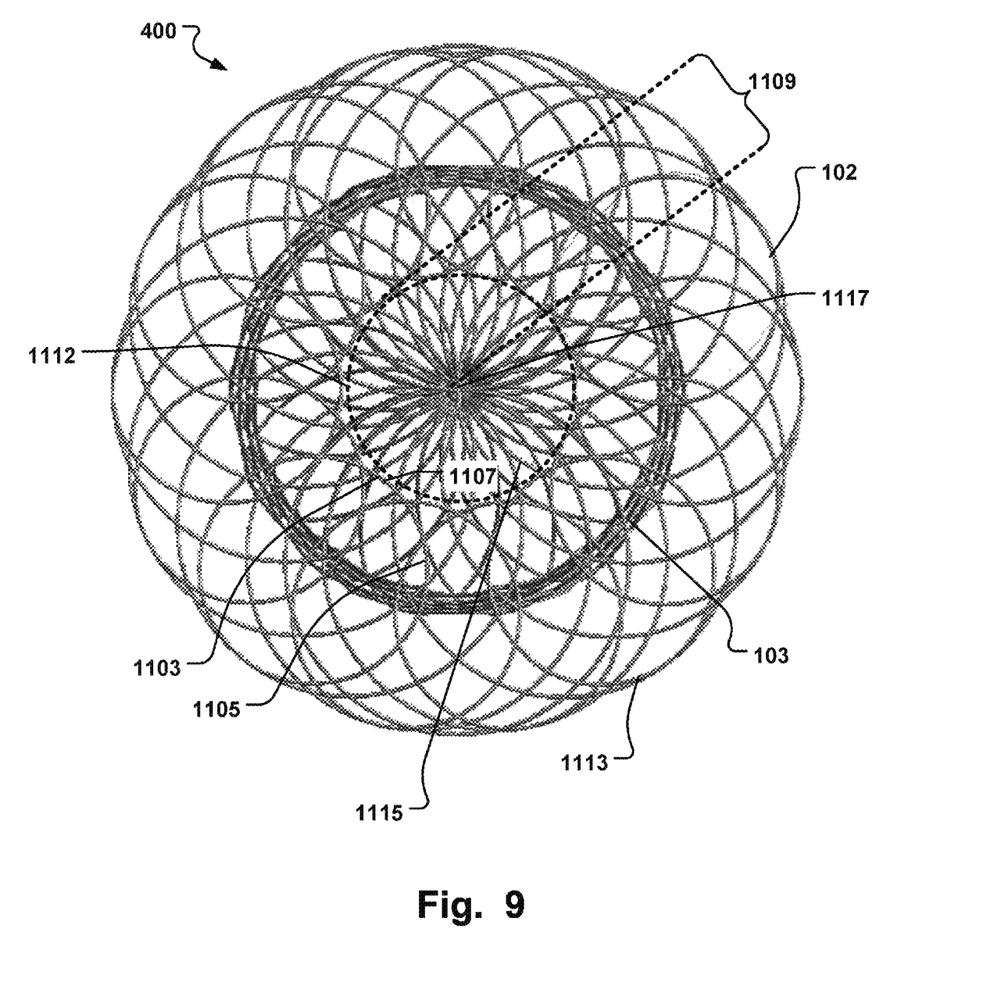
FIG. 9 is an illustration of a medical implantable occlusion device according to an embodiment of the invention in a top down view.

FIG. 3 is a top down view of the device 100 showing the continuous closed braiding of the distal surface 180, and FIG. 4 is a perspective view the device 100. FIG. 9 shows a top-down view of a device 400 according to another embodiment of the invention. The braiding of the expanded diameter portion 102 that is shown in FIG. 9 comprises loops 1103, formed by loop strands 1105 of the least one thread, that returns to the proximal portion 106. Apex points 1107 of each of the loop strands corresponds to the turning point of the loop strands and to the point of each of the loop strands being arranged closest to a centre point 1117 of the expanded diameter portion 102. The apex points are positioned intermediate between the centre point 1117 and a periphery 1113 of the expanded diameter portion. This way less wires will cross the centre 1117 of the expanded diameter portion and the flexibility of the expanded diameter portion will increase so that it can conform freely to different anatomies with less retention force. The remaining parts of the device 400 corresponds to those described in relation to FIGS. 2-5 and 7. The increased flexibility may be advantageous when delivering the device 400 to e.g. a PDA.

Returning to FIG. 9, at least one of the loop strands is displaced from the centre point by a centre distance 1109 and the apex points lie at a distance from the periphery 1113 of the expanded diameter portion that corresponds substantially to the radius of the expanded diameter portion minus the centre distance. The centre distance may vary, such as from ¼th to ¾th of the radius, to allow for different degrees of flexibility. If the loop strands return to the proximal end at a larger distance from the centre point 1117, the flexibility may increase due to less wires at the expanded diameter portion 102 that exert a restraining force.

The loop strands form loops 1103 that may have a curved shape being concave radially outwards from the apex point 1107 to the periphery 1113. The curved shape may extend in a plane being substantially perpendicular to the longitudinal axis 104 of the device, at least in the relaxed state of the device. Thereby the curved loop strands may extend substantially in the plane spanned by the expanded diameter portion. The curved loop strands thereby help to provide the structural framework of the braid at the expanded diameter portion, that assist in holding the device in place at the target site, while allowing increased flexibility as they do not extend across the whole expanded diameter portion, e.g. in particular not across the centre. Of 30 wires, 20 may be looped back, and 10 may extend across the centre.

The centre strands 1115 improves the stability of the device, and/or occlusion effectiveness, while the flexibility and small cross-section is maintained in the collapsed state due to the loop strands being displaced from the centre point 1117. The cross-section of the entire device 400 may be reduced by the displacement of strands from the center 1117. By provision of a smaller cross-section the device 400 may be delivered to a target site in a patient through a delivery device with a reduced cross-section, which may lead to an easier delivery procedure or manipulation of the delivery device in the patient.

Further thanks to the displacement of the loop strands 1105 from the centre point 1117 the amount of force required to compress the device from the expanded state, to the collapsed state, is reduced. This is thanks to the fact that the loop strands 1105 do not cross the centre point 1117. Thus, the amount of threads that must be bent at the centre point 1117 when compressing the device 300 is reduced. Each thread crossing the centre point 1117 or a region close to the centre point 1117 that is subjected to substantial deformation when compressing the device 400 to the collapsed state has a certain amount of structural integrity and an associated force that must be exceeded in order to deform the thread. By having several loop strands 1105 displaced from the region subjected to the most of the deformation, e.g. the centre point 1117, the force required for deformation is thus substantially reduced. A more flexible braided device 400 is thus obtained, which for example can be more easily retracted into a catheter sheath and which exerts less frictional force on the walls of the catheter thereby increasing the ease of operation of the device 400 in the catheter, for example during push and pull motion.

Figure 8:
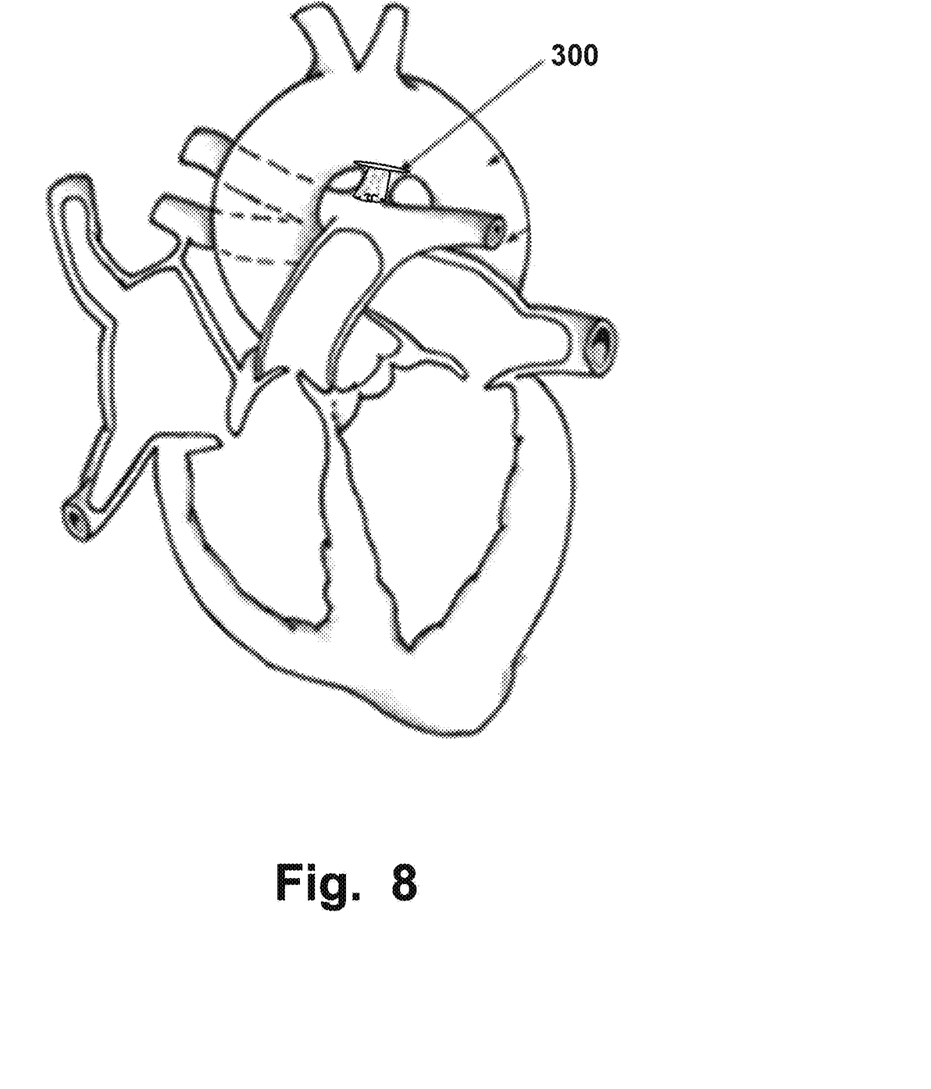
FIG. 8 is an illustration of occluding a PDA in the heart with a medical implantable occlusion device according to an embodiment of the invention.
Figure 10:
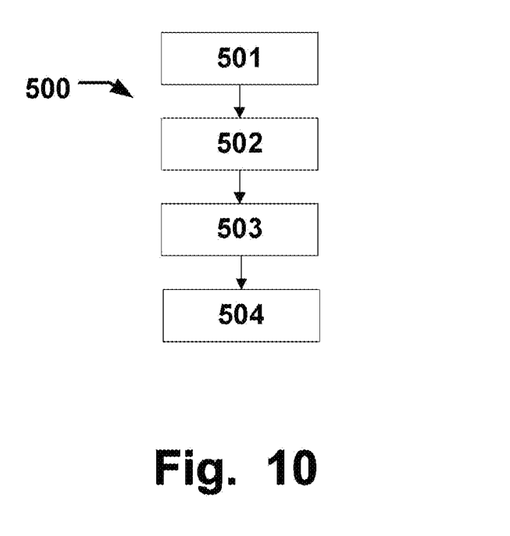
FIG. 10 is a flow chart illustrating a method of occluding an opening in a cardiovascular system with a medical implantable occlusion device according to an embodiment of the invention.

FIG. 10 illustrates a medical method 500 of occluding an opening in a cardiovascular system, comprising providing 601 a device 100-400 as described above, inserting 602 the device 100-400 in a collapsed state into the opening, expanding 603 and releasing the device 100-400 in the opening, thus anchoring 604 the device 100-400 in the opening for occluding the latter by the device 100-400. The opening may be a transapical access opening as illustrated in FIG. 6. In one embodiment the opening may also be a Patent Ductus Arteriosus (PDA), using a device 300 as illustrated in FIG. 7 to occlude the PDA as illustrated in FIG. 8. The device 300 in FIG. 7 may comprise all of the previously discussed features in relation to FIGS. 2-5, but may be particularly customized to occlude a PDA, such as customization of the sizes of the device elements, or occluder flexibility, e.g. by forming the device 300 of a braiding as described in relation to FIG. 9. Patent ductus arteriosus (PDA), which is essentially a condition wherein two blood vessels, most commonly the aorta and pulmonary artery adjacent the heart, have a blood flow shunt between their lumens. Blood can flow directly between these two blood vessels through the passageway, compromising the normal flow of blood through the patient's vessels. Other physiologic conditions in the body occur where it is also desirous to occlude a vessel, a shunt between vessels, or an ostium at a branch vessel, in order to prevent blood flow through the vessel.

Figure 11:
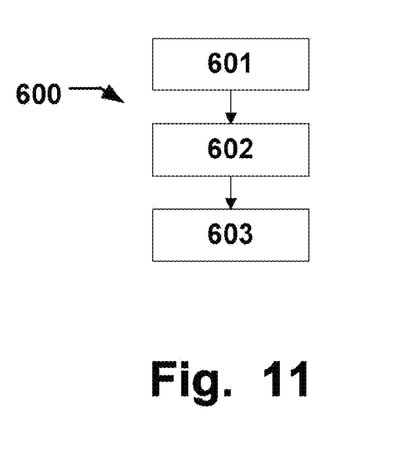
FIG. 11 is a flow chart illustrating a method of occluding a transapical access opening with a medical implantable occlusion device according to an embodiment of the invention.

FIG. 11 illustrates a medical method 600 of occluding a transapical access opening comprising creating 601 an opening in the apex 20 of the heart ventricle 22, performing 602 a procedure through the transapical access, inserting 603 an occlusion device, for example a device 100-400, in the opening to occlude the opening.

The procedure may be a aortic valve reoperation, or a Mitral valve and annulus repair/replacement and reoperation, or ablation of arrhythmia foci in cardiac chambers, or Left atrial appendage closure, or aortic endo-grafting for aneurysms, or percutaneous coronary intervention, or VSD closure, or ablative LA and LV procedures.

The present invention has been described above with reference to specific embodiments. However, other embodiments than the above described are equally possible within the scope of the invention. The different features and steps of the invention may be combined in other combinations than those described. The scope of the invention is only limited by the appended patent claims. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used.

The invention claimed is:

1. A medical implantable occlusion device comprising a braiding of at least one thread, said braiding having an unloaded relaxed state and a stretched state and comprising
    an expanded diameter portion spanning a distal surface forming the distal end of said device, wherein said braiding is continuous at said distal surface,
    a tubular member extending along a longitudinal axis, said tubular member having a distal portion transitioning into said expanded diameter portion at a distal end of the tubular member and an opposite proximal portion at a proximal end of the tubular member,
    wherein said tubular member is continuously tapered from said proximal portion to said distal portion and towards said expanded diameter portion along said longitudinal axis;
    wherein said distal portion transitions to a periphery of said expanded diameter portion with a continuously increasing diameter along said longitudinal axis.

2. Occlusion device according to claim 1, wherein said proximal portion comprises a connecting member for a delivery device, wherein ends of said at least one thread are fixed to said connecting member, and wherein said expanded diameter portion comprises returning loops of said at least one thread whereby opposite ends of said at least one thread forming said expanded diameter portion are fixed to said connecting member.

3. Occlusion device according to claim 2, wherein said connecting member is recessed into said tubular member.

4. Occlusion device according to claim 1, comprising at least one planar and/or voluminous occluding member at the interior or exterior of the tubular member to occlude blood flow.

5. Occlusion device according to claim 1, wherein said expanded diameter portion is flexible with respect to said tubular member such that said expanded diameter portion is moveable with an angle in relation to said longitudinal axis.

6. Occlusion device according to claim 1, wherein said expanded diameter portion is concentric with respect to said tubular member.

7. Occlusion device according to claim 1, wherein said tubular member is tapered such that a ratio is set by dividing a maximum diameter of said proximal portion with a maximum diameter of said distal portion, wherein said ratio is set to a value more than 1.1.

8. Occlusion device according to claim 1, wherein said tubular member and said expanded diameter portion are elastically stretchable relative to each other along said longitudinal axis whereby said device is self-contracting.

9. Occlusion device according to claim 1, wherein said expanded diameter portion is a disc shaped portion, and wherein the diameter of said expanded diameter portion is larger than a largest diameter of said tubular member.

10. A medical method of occluding an opening in a cardiovascular system, comprising
    providing a device of claim 1,
    inserting said device in a collapsed state into said opening,
    expanding and releasing said device in said opening, thus anchoring said device in said opening for occluding the latter by said device.

11. The method of claim 10, wherein said opening is a transapical access opening or a Patent Ductus Arteriosus (PDA).

12. A medical implantable occlusion device comprising a braiding of at least one thread, said braiding having an unloaded relaxed state and a stretched state and comprising
    an expanded diameter portion spanning a distal surface forming the distal end of said device, wherein said braiding is continuous at said distal surface,
    a tubular member extending along a longitudinal axis, said tubular member having a distal portion transitioning into said expanded diameter portion at a distal end of the tubular member and an opposite proximal portion at a proximal end of the tubular member,
    wherein said tubular member is continuously tapered from said proximal portion to said distal portion and towards said expanded diameter portion along said longitudinal axis;
    wherein said expanded diameter portion comprises loops, formed by loop strands of said at least one thread, whereby an apex point of each of said loop strands corresponds to a turning point of said loop strands and to the point of each of said loop strands being arranged closest to a centre point of said expanded diameter portion, and
    wherein said apex points are positioned intermediate between said centre point and a periphery of said expanded diameter portion, wherein said distal end is closed by a plurality of centre stands of said braiding crossing each other at said centre point.

13. A medical method of occluding a transapical access opening comprising:
    providing a device of claim 12,
    creating an opening in the apex of the heart ventricle,
    performing a procedure through the transapical access,
    inserting the occlusion device in said opening to occlude said opening.

14. The method of claim 13, wherein said procedure is an aortic valve reoperation, or a Mitral valve and annulus repair/replacement and reoperation, or ablation of arrhythmia foci in cardiac chambers, or Left atrial appendage closure, or aortic endo-grafting for aneurysms, or percutaneous coronary intervention, or VSD closure, or ablative LA and LV procedures.

15. A medical method of occluding an opening in a cardiovascular system, comprising:
    providing a device of claim 12,
    inserting said device in a collapsed state into said opening,
    expanding and releasing said device in said opening, thus anchoring said device in said opening for occluding the latter by said device.

* * * * *